United States Patent

Ciana et al.

[11] Patent Number: 5,873,812
[45] Date of Patent: Feb. 23, 1999

[54] METHOD OF PREPARING BIOLOGICAL IMPLANTATION MATERIAL

[75] Inventors: Leopoldo Della Ciana, Ravenna; Stefano Rinaldi, Parma; Andrea Grignani; Silvia Pascale, both of Turin, all of Italy

[73] Assignee: Sorin Biomedica Cardio S.p.A., Saluggia, Italy

[21] Appl. No.: 818,783

[22] Filed: Mar. 11, 1997

[30] Foreign Application Priority Data

Mar. 12, 1996 [IT] Italy ................. TO96A0178

[51] Int. Cl.⁶ .................................... A61F 2/04
[52] U.S. Cl. ................... 600/36; 623/2; 623/11; 8/94.11
[58] Field of Search .................. 623/2, 11; 600/36; 8/94.11

[56] References Cited

U.S. PATENT DOCUMENTS

| | | | |
|---|---|---|---|
| 4,383,832 | 5/1983 | Fraefel et al. | 8/94.11 |
| 4,729,139 | 3/1988 | Nashef | 623/2 |
| 4,885,005 | 12/1989 | Nashef et al. | 623/2 |
| 4,976,733 | 12/1990 | Girardot | 8/94.11 |
| 5,188,834 | 2/1993 | Grimm et al. | |
| 5,697,972 | 12/1997 | Kim et al. | 623/2 |
| 5,782,931 | 7/1998 | Yang et al. | 8/94.11 |

*Primary Examiner*—Paul B. Prebilic
*Attorney, Agent, or Firm*—Popovich & Wiles, P.A.

[57] ABSTRACT

A method of preparing biological implantation material fixed by means of aldehydes, in which the excess aldehyde is bound by treatment with an aminocarboxylic acid and the acid is selected from compounds of the general formula:

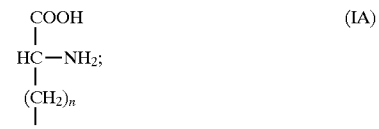

(IA)

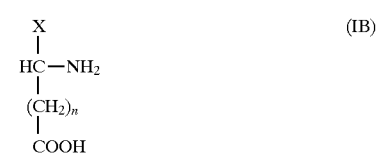

(IB)

in which n is 1 or 2 and X is a sulpho- (—SO₃H) or phosphono- (—PO₃H) group, and mixtures of such compounds.

9 Claims, No Drawings

METHOD OF PREPARING BIOLOGICAL IMPLANTATION MATERIAL

DESCRIPTION

The present invention relates to a method of preparing biological implantation material, in which the material to be implanted is fixed with an aldehyde and the excess aldehyde is bound by treatment with an aminocarboxylic acid.

The use of biological tissues of various origins in the preparation of prosthetic devices is now established in various fields of medicine. The source of the material used for this purpose may vary with regard to both tissue type (heart valves, pericardium, tendons, ligaments, dura mater, skin, veins, etc.) and animal species (autologous, homologous or heterologous tissue).

During the preparation of these devices, it is necessary to use chemical treatments in order permanently to reduce the antigenic properties of these tissues, and hence the possibility of rejection, and to improve their mechanical properties.

Amongst the substances most widely used for fixing biological materials are aldehydes. In particular, glutaraldehyde, formaldehyde, the glyoxals and other aldehydes are used. These compounds can create networks of bonds which stabilize the tissue and glutaraldehyde and formaldehyde in particular are known for their sterilizing effect.

However, adverse effects such as cytotoxicity, the inducing of mineralization, the development of inflammatory reactions, etc., are ascribed to these compounds and to the derivatives which they generate during fixing. In fact, many authors have described the presence of aldehyde residues as one of the main contributory causes of tissue calcification which phenomenon causes, for example, in biological heart-valve prostheses, most of the complications which can be attributed directly to the prosthesis.

The formation of calcium deposits can in fact cause a reduction in the flexibility of the valve flaps and may lead to tearing of the tissue, causing a partial or total reduction in the functionality of the valve.

It is known that glutaraldehyde, like other aldehydes, can react with the amino-residues of amino-acids. However, in the case of proteins, the chemical nature of the products is complex and is not fully understood. The simplest known reaction between an aldehyde group of glutaraldehyde and the amino-residues of lysine leads to the formation of imines. However, the oligomeric and polymeric products which glutaraldehyde generates in a neutral or alkaline environment can also bind to free amino groups of the proteins.

As well as leading to the formation of simple imino-bonds which are generally considered to be reversible with an acid pH, this extensive reactivity also leads to the formation of the more stable β-conjugated imines with positively-charged cyclic structures of the pyridine type.

In order to detoxify biological materials treated with glutaraldehyde, in the past it has been proposed to block the remaining free aldehyde groups with molecules of various kinds. In particular, U.S. Pat. No. 5,188,834 describes the use of dicarboxylic amino-acids in an acid medium for this purpose.

The treatment has to take place with an acid pH. The oligomers and the polymers of glutaraldehyde in fact tend to return to the monomeric form and thus to be removed; moreover, the chemical species generated in the course of the treatment are thought to be β-unsaturated imines which are favoured by the slightly acid pH.

For better control of the pH, the reaction is brought to a conclusion in buffers set at about pH 3.0, such as sodium citrate/HCl, potassium hydrogen phthalate/HCl, citric acid/phosphate, and citrate-phosphate-borate/HCl; on the other hand, use may be made of the buffering effect of the amino-acids themselves in order to keep within the desired pH range.

The subject of the present invention is a method of the type mentioned in the introduction to the present description, characterized in that the excess aldehyde is bound with the use of a compound having the general formula:

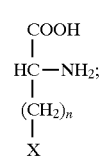

(IA)

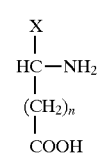

(IB)

in which n is 1 or 2 and X is a sulpho- (—SO$_3$H) or phosphono- (—PO$_3$H) group, or a mixture of such compounds. Since the compounds used according to the invention are more soluble than the dicarboxylic amino-acids used according to the prior art, the preparation and handling of the solutions during the process are radically simplified; in fact the compounds can be dissolved quickly at ambient temperature and there is also a drastic reduction in the volumes used per unit of tissue treated, ensuring an ample excess of reagent.

Amongst the compounds mentioned, 2-amino-3-sulphopropionic acid (cysteic acid), 2-amino-4-sulphobutyric acid (homocysteic acid), 2-amino-3-phosphonopropionic acid and 2-amino-4-phosphonobutyric acid are preferred; amongst these, homocysteic acid is particularly preferred.

Since the compounds concerned have chiral centres, within the scope of the invention, the compounds may be used in the racemic (D, L) form, or in the (L) or (D) form.

The practical advantages of the compounds used according to the invention which result from better solubility, are accompanied by detoxification properties no worse than those of the compounds used conventionally. The effectiveness of the method has been checked both with cell cultures in vitro and in tests on animals (subcutaneous and intramuscular implantation in rats; carotid and valve-replacement implantation in sheep); calcification seems to be reduced, whilst histotoxicity is comparable. Moreover, it can be predicted, with particular reference to the preferred compounds of cysteic acid and homocysteic acid, that these will be less thrombogenic.

Treatment with the compounds according to the invention is carried out with aqueous solutions preferably having a pH within the range from 2.5 to 5.5 and, more particularly, between 3 and 5; the reaction medium is preferably constituted by a buffered medium, preferably belonging to the group of sodium citrate/HCl, potassium hydrogen phthalate/HCl, citric acid/phosphate, and citrate-phosphate-borate/HCl. The concentration of the acid solutions is generally within the range from 10 mM to a saturated solution, particularly, in the case of homocysteic acid, from 10 mM to 273mM (50 g/l).

After treatment, the implantation material is preserved in a biologically compatible sterilizing solution for which a Paraben solution (0.02% n-propyl-p-hydroxy-benzoate and 0.18% methyl-p-hydroxybenzoate) is particularly preferred.

EXAMPLE

Bovine pericardium obtained from the local abattoir was placed in physiological solution with ice. Within one hour it was transferred to the laboratory for the scrupulous removal of fatty residues and connective tissue, again working in 0.9% saline solution and ice. The pericardium was then placed in 0.5% glutaraldehyde solution (pH 7.4) at 4° C. for 48 hours. A portion of this pericardium was sent for normal processing in 4% formaldehyde solution and was then preserved in 0.5% glutaraldehyde; a second batch, however, was washed three times for 20 minutes in physiological solution and was then treated twice for 24 hours in a 59 mM homocysteic acid solution prepared with an approximately 50 mM sodium citrate/HCl buffer, pH 3.3. When the 48 hours had elapsed, the washings with physiological solution were repeated and the product was stored in a Paraben solution.

Various samples were extracted from the pieces of pericardium treated for subcutaneous and intramuscular, that is non-orthotopic, implantation tests in rats, in accordance with an animal model used many times for inducing dystrophic calcification of heterologous tissues, and in investigating tissue reactivity.

For this purpose, 180–220 g Sprague-Dawley rats were selected and four 12 mm-diameter discs per animal were implanted, of which two (one treated and one control) were subcutaneous and two (one treated and one control) were intramuscular.

The animals were killed in accordance with three different implantation periods: 2, 4 and 8 weeks. The explanted samples were processed in order to be subjected to quantitative calcium determination (atomic absorption) and histological and microscopic observation.

The values in μg of Ca/mg of tissue of the various samples are summarised in the table.

Moreover, from the histological tests, no particular tissue reactivity was displayed macro- or microscopically.

| TREATMENT | FOLLOW-UP | Ca (μg/mg dry tissue) |
|---|---|---|
| homocysteic | 14 days | 0.9 ± 0.8 |
| standard | 14 days | 0.6 ± 0.3 |
| homocysteic | 28 days | 1.2 ± 1 |
| standard | 28 days | 64 ± 7 |
| homocysteic | 56 days | 3.8 ± 6 |
| standard | 56 days | 79 ± 9 |

What is claimed is:

1. A method of preparing a fixed biological implantation material comprising (a) fixing a biological implantation material with an aldehyde and (b) treating the fixed biological implantation material with an aminocarboxylic acid in a reaction medium, wherein the aminocarboxylic acid is selected from the group consisting of:

in which n is 1 or 2 and X is —SO$_3$H or —PO$_3$H, and mixtures thereof.

2. A method according to claim 1, wherein the aminocarboxylic acid is selected from the group consisting of 2-amino-4-sulphobutyric acid, 2-amino-4-phosphonobutyric acid, 2-amino-3-sulphopropionic acid and 2-amino-3-phosphono-propionic acid.

3. A method according to claim 1, wherein the reaction medium is an aqueous solution which has a pH within the range from 2.5 to 5.5.

4. A method according to claim 1, wherein the reaction medium is a buffered medium selected from citrate/HCl, potassium hydrogen phthalate/HCl, citric acid/phosphate, and citrate-phosphate-borate/HCl.

5. A method according to claim 1, wherein the reaction medium is an aqueous solution.

6. A method according to claim 1, wherein the aminocarboxylic acid is homocysteic acid.

7. A method according to claim 1, wherein after step (b), the biological implantation material is preserved in a biologically-compatible sterilization solution.

8. A method according to claim 1, wherein the reaction medium is an aqueous solution which has a pH within the range from 3 to 5.

9. A method according to claim 6, wherein the reaction medium is an aqueous solution and the homocysteic acid is at a concentration from 10 mM to 273 mM.

* * * * *